(12) United States Patent
Richardson et al.

(10) Patent No.: US 7,509,172 B2
(45) Date of Patent: *Mar. 24, 2009

(54) STABILIZING GUIDE WIRE APPARATUS FOR USE WITH IMPLANTABLE DEVICE

(75) Inventors: Mark Richardson, Escondido, CA (US); David Anderson, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 765 days.

This patent is subject to a terminal disclaimer.

(21) Appl. No.: 10/421,213

(22) Filed: Apr. 23, 2003

(65) Prior Publication Data

US 2004/0215298 A1  Oct. 28, 2004

(51) Int. Cl.
*A61N 1/05* (2006.01)
(52) U.S. Cl. .................................................... 607/119
(58) Field of Classification Search ................ 607/126, 607/116, 122, 115, 119; 606/213
See application file for complete search history.

(56) References Cited

U.S. PATENT DOCUMENTS

| | | | |
|---|---|---|---|
| 4,209,019 A | 6/1980 | Dutcher et al. | |
| 4,574,800 A | 3/1986 | Peers-Trevarton | |
| 4,884,579 A * | 12/1989 | Engelson | 600/585 |
| 5,003,992 A | 4/1991 | Holleman et al. | |
| 5,011,482 A | 4/1991 | Goode et al. | |
| 5,013,310 A | 5/1991 | Goode et al. | |
| 5,129,404 A | 7/1992 | Spehr et al. | |
| 5,207,683 A | 5/1993 | Goode et al. | |
| 5,234,437 A * | 8/1993 | Sepetka | 606/108 |
| 5,769,858 A | 6/1998 | Pearson et al. | |
| 5,843,141 A | 12/1998 | Bischoff et al. | |
| 5,931,861 A | 8/1999 | Werner et al. | |
| 6,136,005 A | 10/2000 | Goode et al. | |
| 6,356,791 B1 * | 3/2002 | Westlund et al. | 607/115 |
| 2001/0031941 A1 | 10/2001 | Edwards et al. | |
| 2004/0116849 A1 | 6/2004 | Gardeski | |
| 2004/0215298 A1 | 10/2004 | Richardson et al. | |
| 2004/0243209 A1 | 12/2004 | Jarl et al. | |

* cited by examiner

*Primary Examiner*—George R Evanisko
(74) *Attorney, Agent, or Firm*—Hollingsworth & Funk, LLC

(57) ABSTRACT

An apparatus is usable for guiding and stabilizing a body implantable medical device. The apparatus includes a guide wire with an enlarged distal tip. The enlarged distal tip may include a compliant portion to prevent tissue abrasion or perforation. The implantable device includes an open lumen configured to longitudinally advance along the guide wire. A sleeve is disposed over the guide wire and slidably deployable over the enlarged tip of the guide wire. When the implantable device is in final position, the open lumen encompasses at least part of the enlarged tip of the guide wire. The sleeve can be moved over at least part of the enlarged tip and create an interference between the tip and the open lumen, thereby stabilizing the implantable device.

21 Claims, 2 Drawing Sheets

STABILIZING GUIDE WIRE APPARATUS FOR USE WITH IMPLANTABLE DEVICE

FIELD OF THE INVENTION

The invention relates generally to implantable devices, and, in particular, to an apparatus and method for facilitating implanting of such devices in the anatomy.

BACKGROUND OF THE INVENTION

Modern medical technology has produced a wide range of body implantable devices. These devices can be used for low risk treatment and diagnosis of a wide range of medical conditions. In one example, implantable cardioverter/defibrillators (ICDs) are well-known and effective devices for treating patients with cardiac rhythmic dysfunction. A typical ICD includes a pulse generator and an electrical lead with an electrode at the tip. The ICD implantation procedure generally takes about two hours and is relatively low risk, as it rarely requires open-heart surgery. Usually, one or two lead wires are placed through a large vein in the chest and threaded down to the inside of the heart. The lead wires are then connected to the pulse generator, which is placed in a pocket under the skin of the patient.

The details of the implantation procedure vary depending on the technique used and the patient's condition, but typically a guiding catheter is introduced through a major blood vessel such as the cephalic vein. The catheter is then moved through the vasculature to locate an access vessel of interest in the heart, such as the coronary sinus ostium. The catheter can be used alone or in combination with a guide wire. After the coronary sinus ostium has been located by the guiding catheter, an ICD lead can be inserted through the catheter and over the guide wire into the coronary sinus or one of its branches.

After the device is successfully planted, the guide catheter must be removed from the patient. This removal operation creates a risk of dislodging the ICD lead because of the forces applied by the retracting catheter against the lead. Needless to say, dislodging the lead would be problematic, as it requires additional time to reseat the lead. Any such time added to the procedure would be needlessly traumatic to the patient.

There is a need for a method and apparatus for securing a newly implanted lead device while a guiding apparatus is removed, thereby reducing procedure time and patient trauma. The present invention fulfills this and other needs, and addresses other deficiencies of prior art implementations and techniques.

SUMMARY OF THE INVENTION

The present invention discloses an apparatus and method that employs a guide wire that includes a locking feature for stabilizing an implantable device. In one embodiment, an apparatus includes a guide wire with an elongated body and a distal end. An enlarged portion is included at the distal end of the guide wire body. The enlarged portion of the guide wire is dimensioned so that an open lumen of the implantable device is passable over the enlarged portion. A sleeve is slidably disposed along the guide wire. The guide wire and sleeve are relatively movable so that a distal portion of the sleeve creates an interference between the enlarged portion of the guide wire and the open lumen of the implantable device.

In one arrangement, the enlarged portion of the guide wire includes a compliant tip and/or a spring with a distal cap. The sleeve may be formed from a thin walled tube. The distal portion of the sleeve may include a compliant polymer portion. In another configuration, the distal portion of the sleeve includes a longitudinally oriented slot. The implantable device may include one or more of a pacing lead, a defibrillation lead, or a sensing lead.

In another embodiment of the present invention, a method of implanting an implantable device in a destination vessel involves advancing a guide wire into the destination vessel. The guide wire has an enlarged distal portion and a sleeve disposed on the guide wire. The guide wire is advanced so that the enlarged distal portion of the guide wire is located in the destination vessel. The implantable device is advanced along the guide wire so that an open lumen of the implantable device encompasses a portion of the enlarged distal portion of the guide wire. The sleeve and the guide wire are relatively moved so that a distal portion of the sleeve creates an interference between the enlarged distal portion of the guide wire and the open lumen of the implantable device. The implantable device is stabilized with the guide wire.

In one aspect of the method, the destination vessel includes a heart vessel. In another aspect of the method, the sleeve is retracted after stabilizing the implantable device so that the interference between the enlarged distal portion and the open lumen of the implantable device is removed. The guide wire is then retracted from the implantable device.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
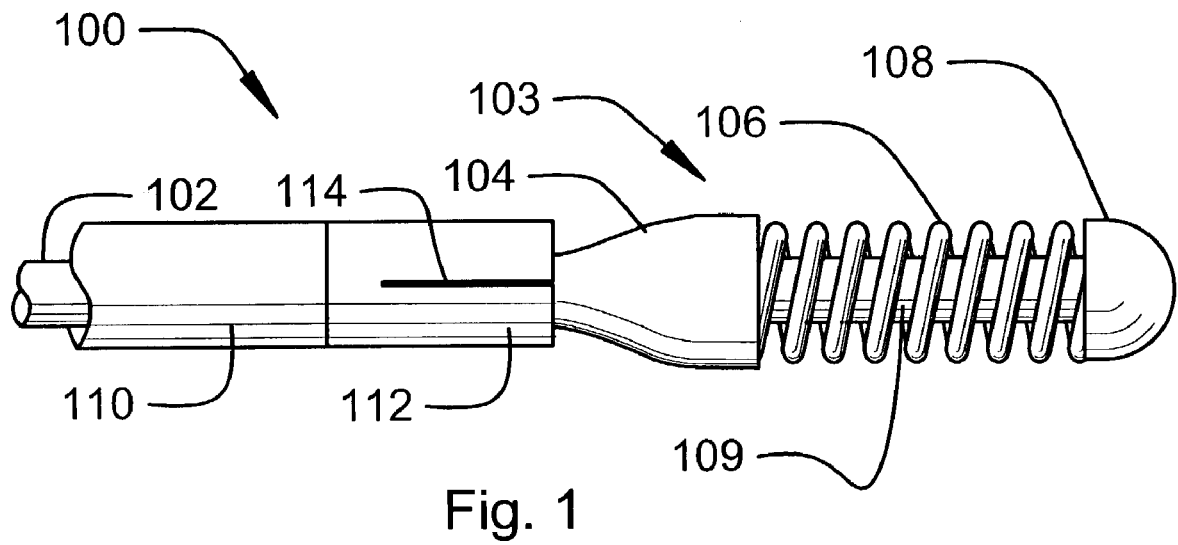
FIG. 1 is a side view of the distal end of a guide wire and sleeve according to embodiments of the present invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, an apparatus and method are disclosed for providing a guide and stabilization member for use with a body-implantable medical device. According to one implementation, an apparatus includes a guide wire that provides a pathway for the implantable device during implantation. A locking feature is employed to stabilize the implantable device while other apparatus are being removed at the end of the procedure. The lockable feature is disengagable so that the apparatus itself can be easily removed. The apparatus is usable with a wide variety of implantable devices, including cardiac pacing and defibrillation leads.

Referring now to the drawings, FIG. 1 shows the distal end of an apparatus 100 for guiding and stabilizing an implantable device. The apparatus 100 includes an elongated guide wire 102. The guide wire 102 is typically formed from a metallic material such as stainless steel (304V) or nitinol (NiTi). The diameter of the guide wire 102 varies depending on the application. In some applications, the proximal part of the guide wire 102 may range from 0.18 mm to 1.0 mm (0.007" to 0.040"). A typical guide wire for cardiac leads may have a diameter ranging from 0.25 mm to 0.51 mm (0.010" to 0.020").

The guide wire 102 includes an enlarged distal end 103. The enlarged distal end 103 is typically made compliant so as to prevent puncturing or abrading tissue when introducing the guide wire 102. When used with a 0.25-0.51 mm guide wire 102, for example, the enlarged distal end 103 may have a diameter ranging from 0.36 mm to 0.64 mm (0.014" to 0.025"). A smooth transition 104 is provided between the proximal part of the guide wire 102 and the enlarged distal end 103. The transition 104 can be formed by any mechanical features known in the art, such as a polymer molding, solder ball, or weld ground to a smooth contour.

The exemplary guide wire 102 shown in FIG. 1 includes a spring member 106 and an end cap 108 at the enlarged distal end 103. In this embodiment, the transition 104 and end cap 108 may encompass part of the spring member 106. The spring member 106 and end cap 108 provide a smooth and compliant tip to the guide wire 102. The end cap 108 may be formed by molding, welding, soldering, etc., and given a smooth finish. A smooth and compliant distal end 103 helps prevent tissue abrasion or perforation.

A core 109 may also be included in the enlarged distal end 103. The core 109 may be an extension of the guide wire body 102, or may be a specialized element. For example, the core 109 may include a shaping member that changes the shape of the enlarged distal end 103. A shaping member may include a super-elastic, shape-retentive member (e.g. a ribbon or wire) that assumes a pre-formed shape above a certain body temperature. The shaping member may include a wire or ribbon that can provide tip steering by manipulating the member at a proximal end of the guide wire.

Although the illustrated exemplary embodiment of the guide wire tip 103 includes a coil spring 106 and smooth end cap 108, it is appreciated that alternate configurations may be used to provide a smooth, compliant distal tip. For example, the enlarged tip 103 may be formed of a rubber or low durometer plastic molding. Typically the enlarged tip 103 will have a smooth, spherical distal tip to prevent tissue trauma.

Also shown in FIG. 1 is a sleeve 110 disposed along the guide wire 102. The sleeve 110 can be fabricated from any member that encompasses at least part of the guide wire 102 and can be slidably moved along the guide wire and up to the enlarged distal tip 103. In the illustrated embodiment, the sleeve 110 is formed from a substantially tubular member.

The sleeve 110 can be constructed of a thin walled metal or polymer tubing having sufficient rigidity to be pushed along the guide wire 102.

The sleeve 110 includes a distal end 112 that is configured to expand when the guide wire's enlarged tip 103 is moved within the distal end 112. The expanded distal end 112 acts to lock the apparatus 100 in a lumen of an implantable device when the distal end 112 is engaged around the enlarged tip 103 of the guide wire 103.

The distal end 112 of the sleeve 110 may be formed from an elastic polymer, such as latex or polyurethane that can expand to encompass the guide wire's enlarged tip 103. A polymer distal end 112 can be bonded, molded, or otherwise fixed to the sleeve 110. Alternative approaches can be used to form a distal end 112 on the sleeve 110 with the desired characteristics. For example, a substantially rigid sleeve 110 may be formed with one or more longitudinal slots 114 at the distal end 112 allowing the tube to expand at the slotted portion. A rigid sleeve 110 may be formed from a metallic or rigid polymer (e.g. polyamide) tubing.

Figure 2:
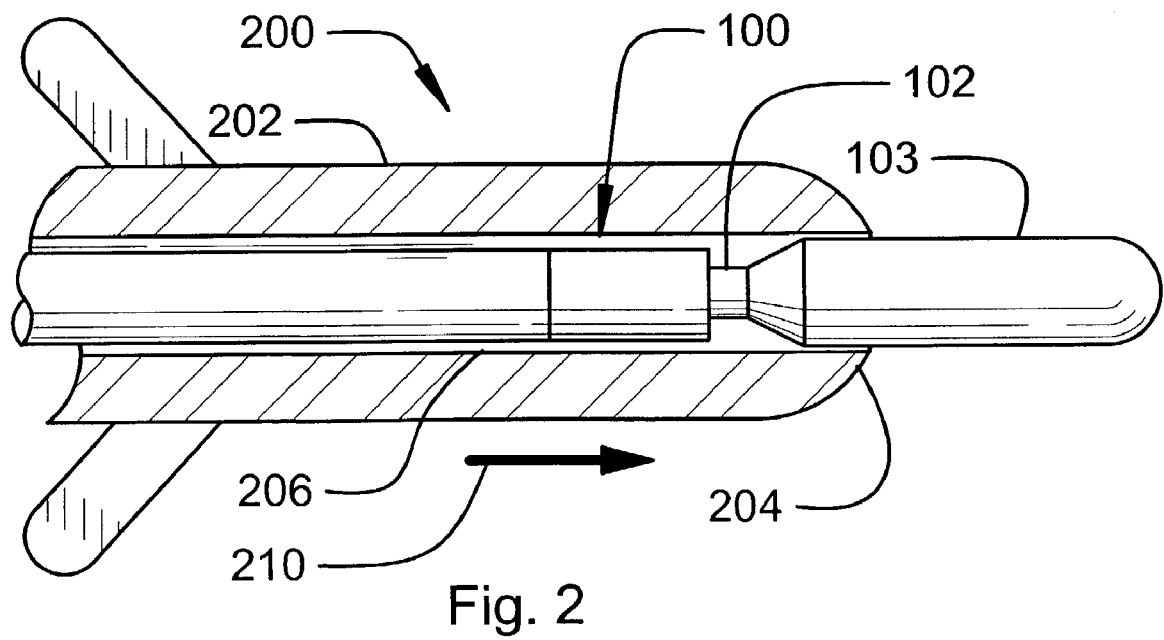
FIG. 2 is a cross-sectional view of an implantable device being placed over the guide wire and sleeve according to embodiments of the present invention.

Turning now to FIG. 2, the apparatus 100 is shown deployed with an implantable device 200. In general, the implantable device 200 is an "over the wire" diagnostic and/or therapeutic device such as pacing lead, defibrillation lead, sensor lead, etc. The implantable device 200 includes a body 202 and an open lumen 206 that includes an opening at the device's distal end 204. The implantable device 200 can be moved over the guide wire 102 as indicated by the bold arrow 210.

The enlarged tip 103 is dimensioned so that it can move freely within the open lumen 206. The open lumen 206 is sized sufficiently to move over the length of the guide wire 102, including the enlarged tip 103. When used with a 0.36 mm to 0.64 mm (0.014" to 0.025") enlarged tip 103, for example, the lumen diameter may range from 0.41 mm to 0.76 mm (0.016" to 0.030").

The implantable device 200 may also be introduced through a guide mechanism such as a guide catheter (not shown) at the same time as being moved over the guide wire 102. The guide catheter is used to direct the implantable device 200 into the general target area, and the guide wire 102 is used to direct the implantable device 200 to its final destination.

Figure 3:
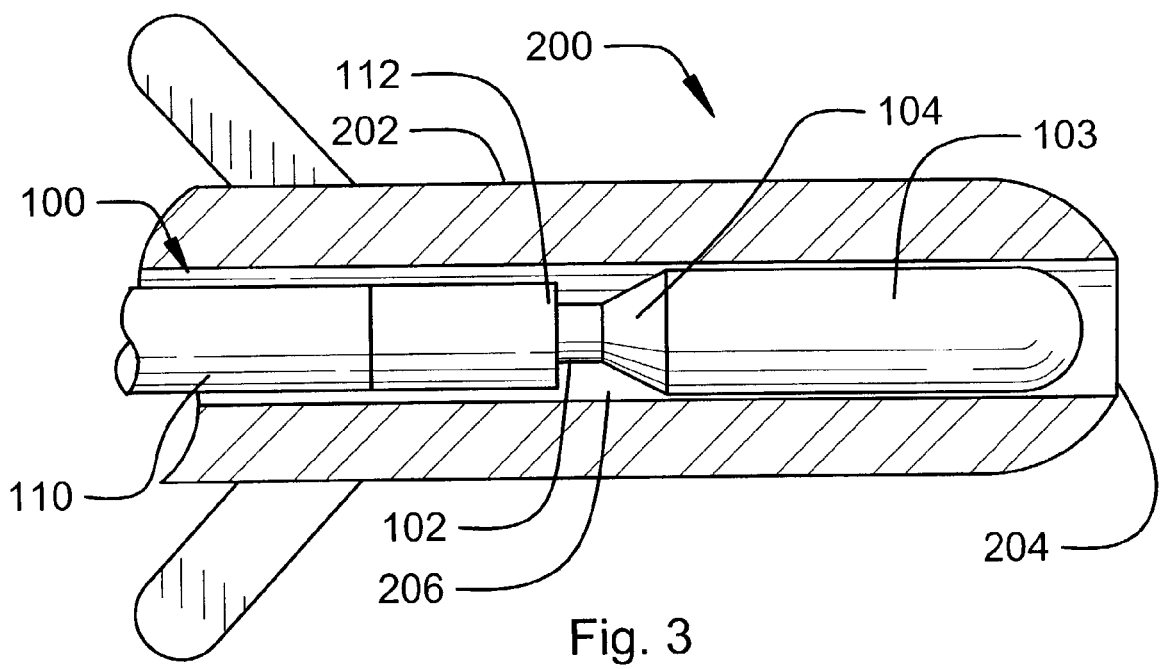
FIG. 3 is a cross-sectional view of the implantable device encompassing the distal end of the guide wire and sleeve according to embodiments of the present invention.

Referring now to FIG. 3, the implantable device 200 and apparatus 100 are shown in an orientation corresponding to the implantable device 200 being located at its final destination. In this orientation, the enlarged tip 103 of the guide wire 102 is at least partly enclosed within the device's lumen 206. After the implantable device 200 is located at its final destination, the guide catheter must be removed. This removal operation has the tendency to dislodge the implantable device 200 due to jostling and longitudinal friction caused by the retracting guide catheter. The apparatus 100 according to the present invention advantageously provides stabilization to the implantable device to prevent dislodgment during guiding catheter extraction.

Figure 4:
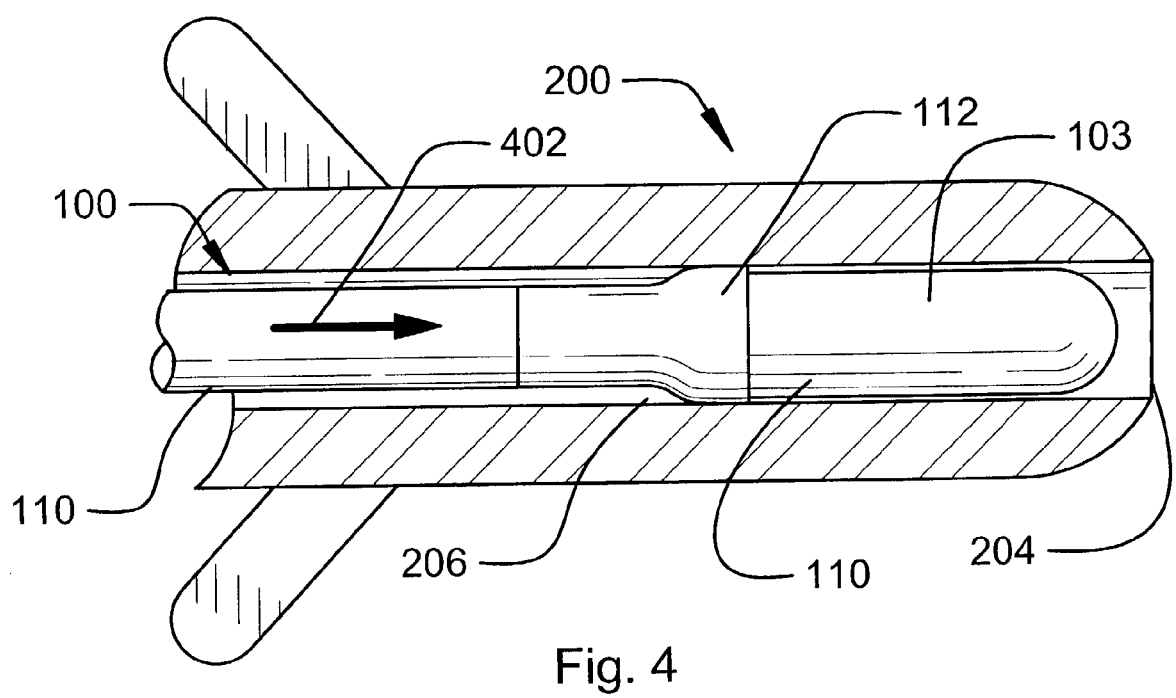
FIG. 4 is a cross sectional view of the implantable device with the sleeve locked in place and forming an interference between the guide wire and the implantable device according to embodiments of the present invention.

A stabilized orientation of the apparatus 100 and implantable device 200 is shown in FIG. 4. To achieve this orientation, the sleeve 110 and guide wire 102 are moved relative to one another so that the distal end 112 moves over a portion of the enlarged tip 103. This relative motion can be achieved by sliding the sleeve in the direction indicated by the bold arrow 402, and/or sliding the guide wire 102 in the direction opposite the bold arrow 402. In this orientation, the distal end 112 of the sleeve forms an interference between the enlarged tip 103 and the lumen 206 of the implantable device 200. This interference mechanically joins the guide wire 102 and implantable device 200 to provide a more stable assembly while the guide catheter or other mechanisms are being removed.

Once guide catheter removal is complete, the apparatus 100 may be removed. This involves pulling back the sleeve 110 opposite the direction indicated by the bold arrow 402 and/or moving the guide wire 102 in the direction of the bold arrow 402. Once the distal end 112 of the sleeve 110 is no longer surrounding the enlarged tip 103 of the guide wire, the apparatus can be easily removed from the implantable device 200.

The movement of the sleeve 110 relative to the guide wire 102 as described in relation to FIG. 4 is typically provided by a device at the proximal end of the apparatus 100. Such proximal devices will typically include attachments to the proximal ends of the guide wire 102 the sleeve 110. The attachments will fixably hold one of the guide wire 102 or sleeve 110 while slidably moving the other. Such attachments that provide this type of relative motion include levers, screws, slides, handles, etc., and are generally well known in the art.

It is appreciated that known techniques used in the manufacture and use of guide wires and similar guiding apparatus are also applicable to the present invention. For example, the guide wire 102 may include additional features such as two adjacent distal coils, radiopaque markers, steering apparatus, alternate cross sectional shapes, and portions formed of alternate materials such as polymers or composites. The guide wire 102 may also include sensing devices such as electrodes, thermal sensors, etc. to assist in implantation procedures.

From the description provided herein, those skilled in the art are readily able to construct and use a stabilizing apparatus and implantable device according to embodiments of the present invention. It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An apparatus for stabilizing an elongated over the wire implantable device having an open lumen, comprising:
    an implantable cardiac lead, the lead having a distal end and a lumen, the lumen open at the distal end of the lead at a distal end opening;
    a guide wire, comprising:
        an elongated body having a distal end; and
        an enlarged portion at the distal end of the elongated body, the enlarged portion and the lead configured such that the lumen of the lead, including the distal end opening of the lumen, is passable over the enlarged portion; and
    a sleeve slidably disposed along the guide wire, the guide wire and the sleeve configured such that relative movement between the guide wire and the sleeve engages the enlarged portion and a distal portion of the sleeve causing the distal portion of the sleeve to expand and engage the lumen of the lead, wherein engagement of the distal portion of the sleeve and the lumen of the lead fixably couples the lead and the guide wire.

2. The apparatus of claim 1, wherein the enlarged portion of the guide wire comprises a compliant tip configured to prevent the guide wire from causing tissue trauma, and wherein the guide wire and the lead are configured such that the guide wire is extendable past the distal end opening of the lead.

3. The apparatus of claim 1, wherein the enlarged portion of the guide wire comprises a spring and a distal cap configured to prevent the guide wire from causing tissue trauma, and wherein the guide wire and the lead are configured such that the guide wire is extendable past the distal end opening of the lead.

4. The apparatus of claim 1, wherein the sleeve comprises a tube configured to radially expand around the enlarged portion of the guide wire upon engagement of the enlarged portion and the tube caused by relative movement between the guide wire and the sleeve.

5. The apparatus of claim 1, wherein the distal portion of the sleeve comprises a compliant polymer portion configured to radially expand around the enlarged portion of the guide wire upon engagement of the enlarged portion and the compliant polymer portion caused by relative movement between the guide wire and the sleeve.

6. The apparatus of claim 1, wherein the distal portion of the sleeve comprises a longitudinally oriented slot.

7. The apparatus of claim 1, wherein the guide wire and the lead are configured such that the guide wire is extendable past the distal end opening of the lead and the guide wire is steerable.

8. The apparatus of claim 1, wherein the guide wire and the lead are configured such that the lumen of the lead, including the distal end opening, can be advanced over the entire length of the guide wire.

9. The apparatus of claim 1, wherein the lumen of the lead has a longitudinally uniform inner diameter defined by an inner surface of the lead, and the guide wire and the lead are configured such that relative movement between the sleeve and the guide wire causes the distal portion of the sleeve to expand and engage the inner surface of the lumen defining the longitudinally uniform inner diameter.

10. An implantable system, comprising:
    an elongated implantable cardiac lead, the lead having a distal end and a lumen, the lumen open at the distal end of the lead at a distal end opening;
    a guide wire comprising:
        an elongated body having a distal end; and
        an enlarged portion at the distal end of the elongated body, the enlarged portion and the lead configured such that the enlarged portion is passable through the lumen and the distal end opening of the lead; and
    a sleeve slidably disposed along the guide wire, the guide wire and the sleeve configured such that relative movement between the guide wire and the sleeve engages the enlarged portion with a distal portion of the sleeve causing the distal portion of the sleeve to expand and engage the lumen of the lead, wherein engagement of the lumen of the lead and the distal portion of the sleeve creates an interference between the enlarged portion of the guide wire and the lumen of the lead that fixably couples the lead and the guide wire.

11. The implantable system of claim 10, wherein the enlarged portion of the guide wire comprises a compliant tip configured to prevent the guide wire from causing tissue trauma, and wherein the guide wire and the lead are configured such that the guide wire is extendable past the distal end opening of the lead.

12. The implantable system of claim 10, wherein the enlarged portion of the guide wire comprises a spring and a distal cap configured to prevent the guide wire from causing tissue trauma, and wherein the guide wire and the lead are configured such that the guide wire is extendable past the distal end opening of the lead.

13. The implantable system of claim 10, wherein the sleeve comprises a tube configured to radially expand around the enlarged portion of the guide wire upon engagement of the enlarged portion and the tube caused by relative movement of the guide wire and the sleeve.

14. The implantable system of claim 10, wherein the distal portion of the sleeve comprises a compliant polymer portion configured to radially expand around the enlarged portion of the guide wire upon engagement of the enlarged portion and the compliant polymer portion caused by relative movement between the guide wire and the sleeve.

15. The implantable system of claim 10, wherein the distal portion of the sleeve comprises a longitudinally oriented slot.

16. The implantable system of claim 10, wherein the guide wire and the lead are configured such that the guide wire is extendable past the distal end opening of the lead and the guide wire is steerable.

17. The implantable system of claim 10, wherein the lumen of the lead has a longitudinally uniform inner diameter defined by an inner surface of the lead, and the guide wire and the lead are configured such that relative movement between the sleeve and the guide wire causes the distal portion of the sleeve to expand and engage the inner surface of the lumen defining the longitudinally uniform inner diameter.

18. The implantable system of claim 10, wherein the guide wire and the lumen of the lead are configured such that the lumen of the lead, including the distal end opening, can be advanced over the entire length of the guide wire.

19. A method of implanting an elongated over the wire implantable cardiac lead in a destination vessel, comprising:

advancing a guide wire having an enlarged distal portion and a sleeve disposed on the guide wire so that the enlarged distal portion of the guide wire is located in the destination vessel;

advancing an implantable cardiac lead having a lumen and a distal end opening of the lumen over the guide wire so that the lumen of the implantable cardiac lead encompasses a portion of the enlarged distal portion of the guide wire;

moving the sleeve and the guide wire relative to one another so that a distal portion of the sleeve expands to create an interference between the enlarged distal portion of the guide wire and the lumen of the implantable cardiac lead, the interference fixably coupling the guide wire and the implantable cardiac lead; and stabilizing the implantable device with the fixably coupled guide wire.

20. The method of claim 19, wherein the lumen of the implantable cardiac lead has a longitudinally uniform inner diameter defined by an inner surface of the implantable cardiac lead and moving the sleeve and the guide wire relative to one another causes the distal portion of the sleeve to expand and engage the inner surface of the lumen defining the longitudinally uniform inner diameter.

21. The method of claim 19, further comprising, after stabilizing the implantable cardiac lead:

moving the sleeve and the guide wire relative to one another so that the interference between the enlarged distal portion and the lumen of the implantable cardiac lead is removed; and retracting the guide wire from the implantable cardiac lead.

* * * * *